United States Patent
Engel et al.

(10) Patent No.: US 10,317,349 B2
(45) Date of Patent: Jun. 11, 2019

(54) X-RAY SCATTER SYSTEMS AND METHODS FOR DETECTING STRUCTURAL VARIATIONS

(71) Applicant: THE BOEING COMPANY, Chicago, IL (US)

(72) Inventors: James E. Engel, Newport Beach, CA (US); Gary Georgeson, Tacoma, WA (US); Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 592 days.

(21) Appl. No.: 14/953,689

(22) Filed: Nov. 30, 2015

(65) Prior Publication Data

US 2017/0153188 A1 Jun. 1, 2017

(51) Int. Cl.
*G01N 23/203* (2006.01)

(52) U.S. Cl.
CPC ..... *G01N 23/203* (2013.01); *G01N 2223/053* (2013.01); *G01N 2223/303* (2013.01)

(58) Field of Classification Search
None
See application file for complete search history.

(56) References Cited

U.S. PATENT DOCUMENTS

| | | | |
|---|---|---|---|
| 5,763,886 A | 6/1998 | Schulte | |
| 7,508,910 B2 | 3/2009 | Safai | |
| 7,529,343 B2 | 5/2009 | Safai | |
| 7,599,471 B2 | 10/2009 | Safai | |
| 7,623,626 B2 | 11/2009 | Safai | |
| 7,649,976 B2 | 1/2010 | Georgeson | |
| 7,835,495 B2 | 11/2010 | Harding | |
| 8,027,427 B2 | 9/2011 | Basu | |
| 8,094,783 B2 | 1/2012 | Harding | |
| 2004/0251415 A1* | 12/2004 | Verbinski | G01N 23/02 250/358.1 |
| 2005/0084064 A1* | 4/2005 | McIntyre | G01N 23/04 378/54 |
| 2009/0168958 A1 | 7/2009 | Cozzini | |
| 2011/0170661 A1* | 7/2011 | Bueno | G01V 5/0008 378/57 |
| 2013/0208850 A1* | 8/2013 | Schmitt | G01N 23/20 378/4 |

(Continued)

OTHER PUBLICATIONS

Extended European Search Report for EP 16187910.1-1559, dated Mar. 24, 2017.

(Continued)

*Primary Examiner* — Hoon K Song
(74) *Attorney, Agent, or Firm* — The Small Patent Law Group, LLC; Joseph M. Butscher (57) ABSTRACT

Embodiments of the present disclosure provide systems and methods for detecting one or more thermal and/or mechanical properties of a structure. The method may include forming one or more test structures from a material that forms the structure, generating and storing calibration data determined from the one or more test structures, emitting X-ray radiation into the structure, detecting X-ray scatter from the structure, and determining the one or more properties of the structure based on the detected X-ray scatter and the calibration data.

19 Claims, 4 Drawing Sheets

(56) References Cited

U.S. PATENT DOCUMENTS

2013/0315376 A1    11/2013    Safai

OTHER PUBLICATIONS

P Zhu, et al: "UTterworth Eineman N In-line density measurement system using X-ray Compton scattering," NDT&E International, Jan. 1995 (Jan. 1995), pp. 3-7.

Kolhoor Sanjeevareddy, et al.: "A new X-ray backscatter imaging technique for non-destructive testing of aerospace materials," NDT&E Internaitonal, vol. 70, Nov. 26, 2014, pp. 41-52.

Poranski, et al: "X-ray backscatter tomography for nondestructive evaluation at the Naval Research Laboratory," Optomechatonic Micro/Nano Devices and Components III:Oct. 2007.

Shedlock: "Optimization of an RSD x-ray backscatter system for detecting defects in the space shuttle external tank thermal foam insulation," SPIE—International Society for Optical Engineering Proceedings, vol. 5923, Aug. 18, 2005.

\* cited by examiner

X-RAY SCATTER SYSTEMS AND METHODS FOR DETECTING STRUCTURAL VARIATIONS

FIELD OF THE DISCLOSURE

Embodiments of the present disclosure generally relate to X-ray scatter systems and methods for detecting variations on or within structural components, and, more particularly, to systems and methods for detecting structural variations through analysis of X-ray scatter data, such as backscatter and/or forward scatter data.

BACKGROUND OF THE DISCLOSURE

Aircraft structures may be formed from composite materials, which are generally reinforced polymer-based materials used in place of metals, particularly in applications in which relatively low weight and high mechanical strength is desired. Composite materials are widely used in a variety of commercial and military aircraft, terrestrial vehicles, and consumer products. A composite material may include a network of reinforcing fibers that are generally applied in layers, and a polymeric resin that substantially wets the reinforcing fibers to form a binding contact between the resin and the reinforcing fibers. The composite material may then be formed into a structural component by a variety of known forming methods, such as an extrusion process or other forming processes.

Variations within composite structures (such as those of an aircraft) may be caused by a lightning strike, fire, engine exhaust, or other high temperature incidents. Incipient heat damage in composites is generally not detectable using typical non-destructive inspection (NDI) techniques, such as ultrasonic methods.

Infrared (IR) spectroscopy is an approved method for detecting variations with respect to components of certain aircraft. However, IR spectroscopy is typically used to detect variations on an outer surface of a structure. In short, IR spectroscopy is unable to effectively determine variations within a structure.

Ultrasonic systems and methods may also be used to detect variations within a structure, such as caused by heat damage. However, a structure may have already significantly changed before the ultrasonic system detects the variation.

Overall, known systems and methods for detecting variations within a composite structure, such as a portion of an aircraft, are generally not effective in detecting incipient heat variations.

SUMMARY OF THE DISCLOSURE

A need exists for a system and a method that are able to effectively detect localized areas of structural variation (such as may be caused by heat damage) within a structure, such as a portion of an aircraft. A need exists for a system and method for quantifying a level of variation to a structure, such as caused by heat. Further, a need exists for a system and a method that are able to detect areas of incipient variation within a composite structure before the variation increases to an undesired level.

With those needs in mind, certain embodiments of the present disclosure provide a method of detecting one or more properties of a structure. The method may include generating and storing calibration data determined from one or more test structures that are formed from a material that forms the structure, emitting X-ray radiation into the structure, detecting X-ray scatter from the structure, and determining the one or more properties of the structure based on the detected X-ray scatter and the calibration data. The properties may be thermal and/or mechanical properties. The X-ray scatter is one or both of X-ray backscatter or X-ray forward scatter. The one or more properties include one or both of a density of the structure, or a variation level of polymeric bonds within the structure. The determining may include associating differences in the density of the structure with levels of variation caused by heat energy.

The method may also include comparing the X-ray scatter to a predetermined threshold to determine areas of variation within the structure. The generating and storing steps may include generating and storing the calibration data as a calibration curve or lookup table. The method may also include generating a variation map from the X-ray scatter data.

Certain embodiments of the present disclosure provide a property detection system configured to detect one or more properties of a structure. The property detection system may include an X-ray assembly including an X-ray source that emits X-ray radiation into the structure, and one or more scatter detectors that detect X-ray scatter that scatter from the structure. The X-ray assembly scans test structure(s) formed of a material that forms the structure. The property detection system may also include a control unit coupled to the X-ray assembly. The control unit generates and stores calibration data determined from the one or more test structures. The control unit determines the properties based on the X-ray scatter and the calibration data.

Certain embodiments of the present disclosure provide a property detection system that may include an X-ray assembly including an X-ray source that is configured to emit X-ray radiation into a structure, and one or more scatter detectors that are configured to detect X-ray scatter that scatter from the structure. The X-ray assembly is configured to scan one or more test structures before emitting the X-ray radiation into the structure. The test structure(s) are formed of a material that forms the structure.

The property detection system may also include a control unit coupled to the X-ray assembly. The control unit is configured to: generate and store calibration data determined from the one or more test structures, determine variation within a structure by determining a density of the structure based on the detected X-ray scatter, associate differences in one or both of the density or polymeric bonds of the structure with levels of variation within the structure, and compare the X-ray scatter to a predetermined threshold to determine areas of variation within the structure.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Embodiments of the present disclosure may be used to inspect various structures, such as composite structures, carbon-carbon structures, plastics, cross-linked polymers, other resin-based structures, and/or the like. Embodiments of the present disclosure may also be used to detect various mechanical and thermal properties internal to a part, such as strength, stress, and/or the like. Additionally, embodiments of the present disclosure may be used during a curing process (of a composite structure, for example), or for determining thermal properties of a structure, such as a heat shield. In short, embodiments of the present disclosure may be used to determine one or more physical properties of a structure through analysis of scatter data.

Certain embodiments of the present disclosure provide systems and methods that are used to determine internal mechanical and/or thermal properties of a material that forms a structure. The internal properties of the material change with varying levels of exposure to heat, for example. As an example, when the structure is exposed to a first temperature, the internal molecular structure has a first characteristic. With increasing temperature, the internal molecular structure changes, such that at a second temperature that is greater than the first temperature, the internal molecular structure has a second characteristic. Embodiments of the present disclosure utilize X-ray scatter to detect the internal variations of the material due to thermal exposure and/or mechanical variations.

Certain embodiments of the present disclosure provide systems and methods for determining thermal and/or mechanical properties of a structure. Further, certain embodiments of the present disclosure provide systems and methods for determining internal thermal and mechanical properties of a structure.

Certain embodiments of the present disclosure provide systems and methods that are configured to quickly and efficiently automatically determine variations and/or properties (such as levels of damage) of a composite structure. Embodiments of the present disclosure provide systems and methods for determining changes of internal mechanical and/or thermal properties of a structure.

The variations and/or properties may include one or more of heat damage, mechanical or structural anomalies, inconsistencies, alterations, or the like. In at least one embodiment, the variations and/or properties may include characteristics or features of the structure. Heat damage or degradation may occur over time to a structure, and may be caused, for example, by lightning strikes Certain embodiments of the present disclosure provide a method of detecting one or more physical properties of a structure that may include scanning a test structure (such as one or more calibration coupons) with an X-ray assembly of a property detection system. The physical properties may be analyzed to determine whether the structure has been changed, such as through application of heat energy. The test structure is formed of a material and has a thickness that is the same or similar to a structure that is to be inspected for variation. For example, the test structure may be formed of a composite material that is used to form a structure, such as a wing of an aircraft. The test structure may include a range of thicknesses that are used to form the structure. The test structure may represent a range of thermal properties (such as no heat damage to maximum heat damage at which the structure disintegrates).

The material used to form the test structure and the structure may include a particular molecular structure, such as polymer chains in a matrix. In general, one or more properties of the molecular structure change in response to application of increasing heat energy. For example, a density of the molecular structure decreases as the structure burns, chars, or the like. Polymeric bonds within or between a matrix degrade at excessive temperature, which may lead to variations in density. The change in molecular structure affects a level of X-ray scatter, such that an intensity of X-ray scatter (for example, a number of X-ray photons that scatter from the structure) is greater in undamaged normal portion (for example, when manufactured as intended) of the structure as compared to a changed portion of the structure. As variation (such as damage) increases at higher temperatures or prolonged heating, oxidation (charring) of the matrix also occurs, which results in density variation and density reduction, which thereby reduces the scatter intensity. In at least one embodiment, a density of a structure may not be significantly affected by heat damage, but scatter reduction associated with damage to molecular chains of a structure may be detected. In at least one embodiment, a control unit may associate thermally-induced changes in polymeric bonds within and between a matrix, which may cause variations in material density.

An X-ray assembly is used to scan the test structure, including the different areas of structural variation, such as different areas of heat damage. X-ray scatter data is correlated with each area of heat damage. For example, an area of no damage is correlated with a first X-ray scatter intensity, an area of a low level of heat damage is correlated with a second X-ray scatter intensity (that is lower than the first X-ray scatter intensity), an area of a medium level of heat damage is correlated with a third X-ray scatter intensity (that is lower than the second X-ray scatter intensity), and so on. The correlated X-ray scatter intensities may be correlated with the varying levels of heat damage (from no damage to maximum heat damage) in a calibration curve, a lookup table, and/or the like.

After the test structure is scanned and used to correlate scatter intensities with thermal properties (such as heat damage), an actual structure (formed of the same material as the test structure) to be inspected may then be scanned by the X-ray assembly. Detected scatter intensities of the structure may be referenced in relation to correlated thermal properties (such as determined through the test structure) to determine specific areas and intensities of heat damage of the structure.

Calibration data (such as calibration curves, lookup tables, and/or the like) collected from the test structure may be automatically applied to a resulting scattered image, creating a two-dimensional map of structural properties or characteristics, such as a map of structural degradation that may be caused by heat. The map may be displayed (in color or grayscale) as percent strength, maximum temperature at nominal time, or another physical property, depending on how the test structure was tested. The variation map may be input into a finite element model of the structure for performance prediction, repair size, geometry determination, and analysis. The variation map may also be used by repair personnel to determine how much damaged material to cut or otherwise remove from a structure and/or how large of an overlay to make. As such, through embodiments of the present disclosure, individuals are able to precisely determine an exact size of a repair material (that is, not too large or too small of a repair material) based on the actual size of the damaged or otherwise compromised area of the material.

Certain embodiments of the present disclosure provide a method for detecting incipient heat damage within a composite part. The method may include irradiating a section of the composite part within an X-ray beam, detecting the scatter (such as backscatter of forward scatter) from the irradiation, and processing the detected scatter to determine areas of incipient heat damage within the composite part.

Figure 1:
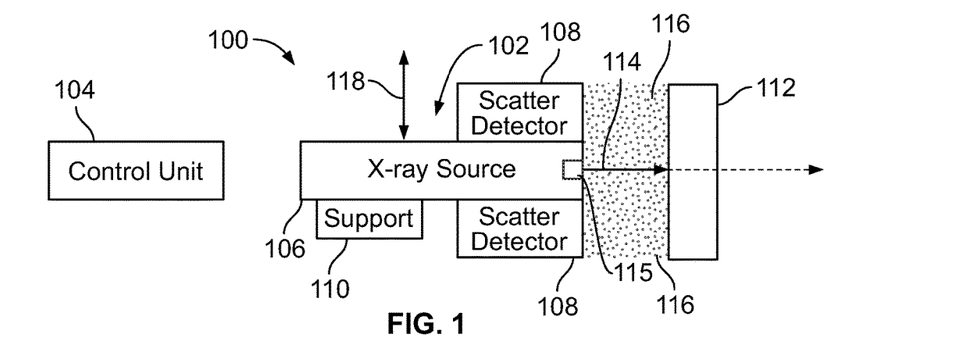
FIG. 1 illustrates a schematic diagram of a property detection system, according to an embodiment of the present disclosure.

FIG. 1 illustrates a schematic diagram of a property detection system 100, according to an embodiment of the present disclosure. The property detection system 100 includes an X-ray assembly 102 operatively coupled to a control unit 104, such as through one or more wired or wireless connections. The property detection system 100 may also include one or more test structures, as described below, such as the test structure 120 shown in FIG. 3.

The X-ray assembly 102 includes an X-ray source 106, such as an X-ray tube, one or more scatter detectors 108 (as opposed to transmission scatter detectors that detect X-rays that pass through a structure), and a support 110. The X-ray source 106 and the scatter detector(s) 108 may be positioned to one side of a composite structure 112 to be inspected. The X-ray source 106 is configured to emit a primary X-ray beam 114 through an aperture 115 into the composite structure 112. As the primary X-ray beam 114 passes into and through the composite structure 112, X-ray photons scatter from the structure 112 and are detected by the scatter detector(s) 108 as X-ray scatter 116, such as backscatter data. The X-ray assembly 102 may alternatively include more or less scatter detectors 108 than shown. For example, the X-ray assembly 102 may include a single scatter detector 108.

The control unit 104 analyzes the X-ray scatter 116 and compares the X-ray scatter 116 to stored calibration or reference data (hereafter referred to as calibration data), such as contained within one or more calibration curves, lookup tables, and/or the like. The stored calibration data may be stored within one or more memories in communication with and/or within the control unit 104. The stored calibration data may correlate various levels of structural variation (such as various levels of heat damage) with corresponding levels of scatter intensity (such as scatter counts). As such, the control unit 104 analyzes the received X-ray scatter 116 and associates the X-ray scatter 116 with structural variation. As the X-ray assembly 102 is moved in relation to the structure, the control unit 104 detects the X-ray scatter 116 from different areas of the structure 112, and determines levels of structural variation at the various areas of the structure by comparing the different intensity levels of the X-ray scatter 116 at the different areas with associated levels of structural variation (such as associated levels of heat damage) stored in the calibration data.

The support 110 may be used to move the X-ray assembly 102 in relation to the structure 112. For example, the support 110 may include one or more rails that retain wheels of a base of the X-ray assembly 102, thereby allowing the X-ray assembly 102 to translate in directions denoted by arrows 118. In at least one other embodiment, the support 110 may include a swiveling base that allows the X-ray assembly 102 to rotate and sweep the primary X-ray beam 114 in relation to the structure 112. The support 110 may include one or more actuators that are configured to automatically move the X-ray assembly 102. Optionally, the X-ray assembly 102 may be configured to be manually moved via the support 110. The X-ray assembly 102 may be moved in relation to the structure 112 such as by being moved manually or automatically on tracks, rollers, or the like.

Figure 2:
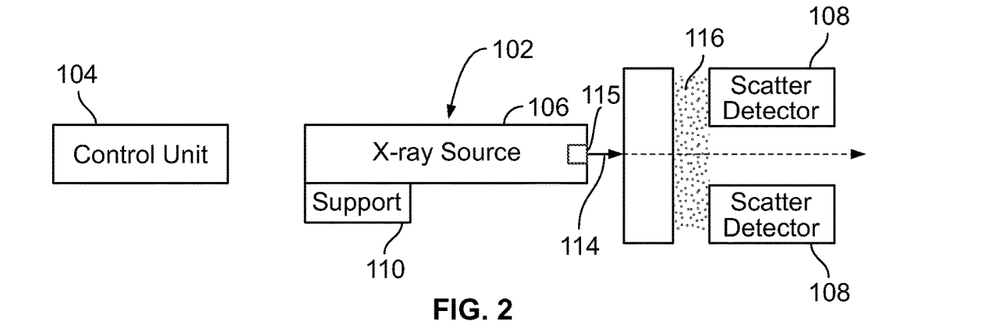
FIG. 2 illustrates a schematic diagram of a property detection system, according to an embodiment of the present disclosure.

FIG. 2 illustrates a schematic diagram of the property detection system 100, having a different configuration than shown in FIG. 1. The property detection system 100 is similar to that shown in FIG. 1, except that the X-ray source 106 is positioned to one side of the structure 112, while the scatter detectors 108 are positioned to an opposite side of the structure 112. The structure 112 to be inspected is disposed between the x-ray source 106 and the scatter detectors 108. As such, the scatter detectors 108 are configured to detect the X-ray scatter 116 as forward scatter data that scatters from the structure away from the primary X-ray beam 114. Alternatively, the property detection system 100 may include scatter detectors 108 on both sides of the structure 112, and may therefore be configured to detect properties of the structure based on both X-ray backscatter and X-ray forward scatter.

Figure 3:
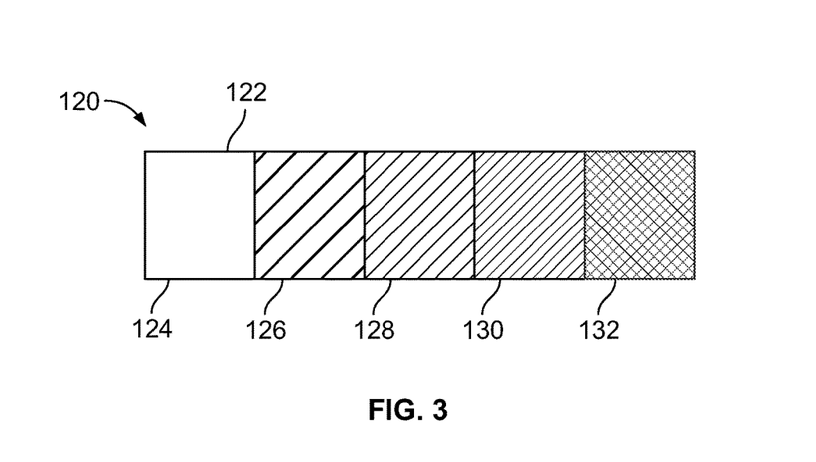
FIG. 3 illustrates a front view of a test structure, according to an embodiment of the present disclosure.

FIG. 3 illustrates a front view of a test structure 120, according to an embodiment of the present disclosure. The test structure 120 may include a strip of material 122 having similar physical properties of the composite structure 112 that is to be inspected. For example, the strip of material 122 may be formed of the same material as the composite structure 112, and may include the same thickness or thicknesses of the composite structure 112. The test structure 120 is tested to provide a correlation between at least one physical property of the structure and scatter intensity. The physical properties may be associated with levels of heating and/or curing of the material 122, for example.

The test structure 120 has known physical characteristics (for example, thickness, material type, and the like), and is subjected to one or more tests for mechanical and/or thermal properties, such as a three-point bend test, a fatigue test, a strength test, a heat test, and/or other mechanical tests. In at least one embodiment, the test structure 120 may be tested at various levels and/or ranges from no or minimal heat-related inconsistencies, anomalies, or other such variations to a maximum level of heat-related inconsistencies, anomalies, or other such variations. For example, the test structure 120 may be tested at various levels or ranges from a minimum variation or property level (such as no damage) to a maximum variation or property level (such as maximum damage) in relation to a particular test.

For example, the test structure 120 may be used in relation to testing a particular structure for heat damage. In this embodiment, the test structure 120 may include a plurality of regions 124, 126, 128, 130, and 132, each of which is subjected to a different level of a test. The region 124 is subjected to no damage (for example, no heat is applied to the region 124). The region 126 is subjected to a low level of damage. The region 128 is subjected to an intermediate level of damage. The region 130 is subjected to a heightened level of damage. The region 132 is subjected to a maximum level of damage. The maximum level of damage may be a level of damage just prior to a structure disintegrating. For example, the maximum level of damage may be a level of damage when delaminations begin to form within a composite part.

The test may be a heat damage test. As such, the region 124 may be subjected to room temperature (for example, no additional heat imparted into the region 124). The region 126 may be subjected to a low level of heat energy that exceeds room temperature. The region 128 may be subjected to an intermediate level of heat energy that exceeds the low level of heat energy. The region 130 may be subjected to a heightened level of heat energy that exceeds the intermediate level of heat energy. The region 132 may be subjected to a maximum level of heat energy that exceeds the heightened level of heat energy, and at which delaminations begin to form within the region 132.

As different levels of test energy (such as heat, stress, strain, and/or the like) are exerted into each region 126-132, physical properties of the regions 126-132 are altered. Different areas within the test structure 120 scatter X-ray radiation differently depending on internal changes that have occurred in the test structure 120. For example, heating a composite part that includes resin, plastic, or other cross-linked polymer(s) changes physical and/or thermal properties of the composite part, which thereby causes X-ray radiation to scatter differently from the areas having different properties.

For example, the test energy (such as heat energy) affects the density of each of each region 124-132 in a different manner. Because no test energy is imparted into the region 124, the density of the region remains the same as normal (for example, undamaged) portion of a structure. However, with increasing levels of test energy, each region 126-132 becomes more damaged. For example, increasing levels of heat energy progressively damage the regions 126-132, such as by reducing densities thereof. As such, each region 124-132 represents a different level of damage caused by a particular test (such as a heat damage test). Optionally, the regions 124-132 may represent different levels of bond degradation of a material. Degraded polymeric chains may scatter less X-ray radiation, and may provide an indication of structural variation (such as caused by heat damage) before the density of the structure is affected due to material loss Each of the regions 124-132 may represent a test coupon. As shown, the regions 124-132 may be connected together in a single strip of material 122. Alternatively, each of the regions 124-132 may be a separate and standalone test coupon that is not connected to another. Optionally, more or less test regions 124-132 than shown may be used.

Referring to FIGS. 1-3, after the test structure 120 has been tested to form the different levels of variation (for example, damage) represented by the regions 124-132, the test structure 120 is scanned by the X-ray assembly 102. As the x-ray source 106 scans (such as rotating through an imaging range, being translated in relation to a structure, and/or the like) the primary X-ray beam 114 over each of the regions 124-132, the X-ray scatter 116 that scatters from the regions 124-132 differs. Because the physical properties of each of the regions 124-132 differ due to the test(s) performed on the test structure 120, each region 124-132 scatters a different amount of the primary X-ray beam 114 as X-ray scatter 116. For example, the region 124 is uncompromised and has a normal density (and/or non-degraded cross-linked polymeric chains), which scatters the most amount of the primary X-ray beam 114 as X-ray scatter 116.

Conversely, the region 132 has been compromised (such as by being damaged through excessive heat energy) the most, and therefore the density of the region 132 is less than the other regions 124-130. As such, the region 132 scatters the least amount of the primary X-ray beam 114 as X-ray scatter 116.

The scatter detectors 108 detect the X-ray scatter 116 from each of the regions 124-132 and the control unit 104 correlates the received X-ray scatter 116 with the known amount of test energy (and therefore the levels of variation) imparted into the regions 124-132. The control unit 104 may correlate data related to the received X-ray scatter 116 from the regions 124-132 with the known levels of variation thereof, and store the correlated data in a memory as calibration data. For example, the control unit 104 may store the calibration data in one or more calibration curves, lookup tables, and/or the like. The calibration data may be stored for each known physical characteristic, test, and scanning parameters for several different test structures. The control unit 104 is then able to compare collected data of an actual structure to be inspected, such as the structure 112, with the calibration data to determine areas of variation within the structure 112.

The structure 112 (such as a composite structure of an aircraft) is scanned by the X-ray assembly 102. The X-ray scatter 116 scattered from various areas of the structure 112 is detected by the scatter detectors 108. The control unit 104 analyzes data received the scatter detectors 108 and compares the received data with the calibration data to determine the extent of structural variation (such as the extent of heat damage) at various areas of the structure 112.

Based on the calibration data, acceptable variation levels (such as acceptable levels of degradation) may be determined. For example, a certain percentage may be set as a variation threshold. In at least one embodiment, 80% of X-ray scatter 116 from a first portion, such as the region 124 (for example, an undamaged portion), may be set as a variation threshold. If the control unit 104 detects less than 80% of the X-ray scatter 116 at a particular area of the structure 112, the control unit 104 may determine that the area may be repaired.

The received X-ray scatter 116 may be representative of internal physical properties of the structure 112. For example, the received X-ray scatter 116 may be representative of a density, flexibility, strength, and/or the like of the structure 112 at any particular point. The physical properties determined through detection of the X-ray scatter 116 allow for an assessment of variation (such as degradation or other such damage) to the structure 112 at various points. For example, decreased density of the structure 112 may represent variation caused by heat energy imparted into the structure 112.

The control unit 104 analyzes scatter data from signals received by the scatter detectors 108, which detect the X-ray scatter 116. Based on the analyzed scatter data, the control unit 104 determines one or more internal physical properties (such as density) of the structure 112 at various locations or along the structure 112. The control unit 104 may compare the analyzed scatter data (as detected from the received X-ray scatter 116) with the calibration data to determine the physical properties. Based on the determined physical properties, the control unit 104 may assess variations in relation to the structure 112.

Alternatively, the control unit 104 may not utilize calibration data to determine physical properties of the structure 112. In such an embodiment, the test structure 120 may not be needed. Instead, the control unit 104 may analyze scatter data detected from X-ray scatter 116 from various locations of the structure 112. The control unit 104 may determine differences in physical properties of the structure 112 at various locations thereof based on differences in scatter data. For example, the control unit 104 may determine irregularities (such as damage or degradation) at a particular location of the structure 112 in which a 20% reduction in X-ray scatter 116 is received in comparison to another location of the structure 112.

Figure 4:
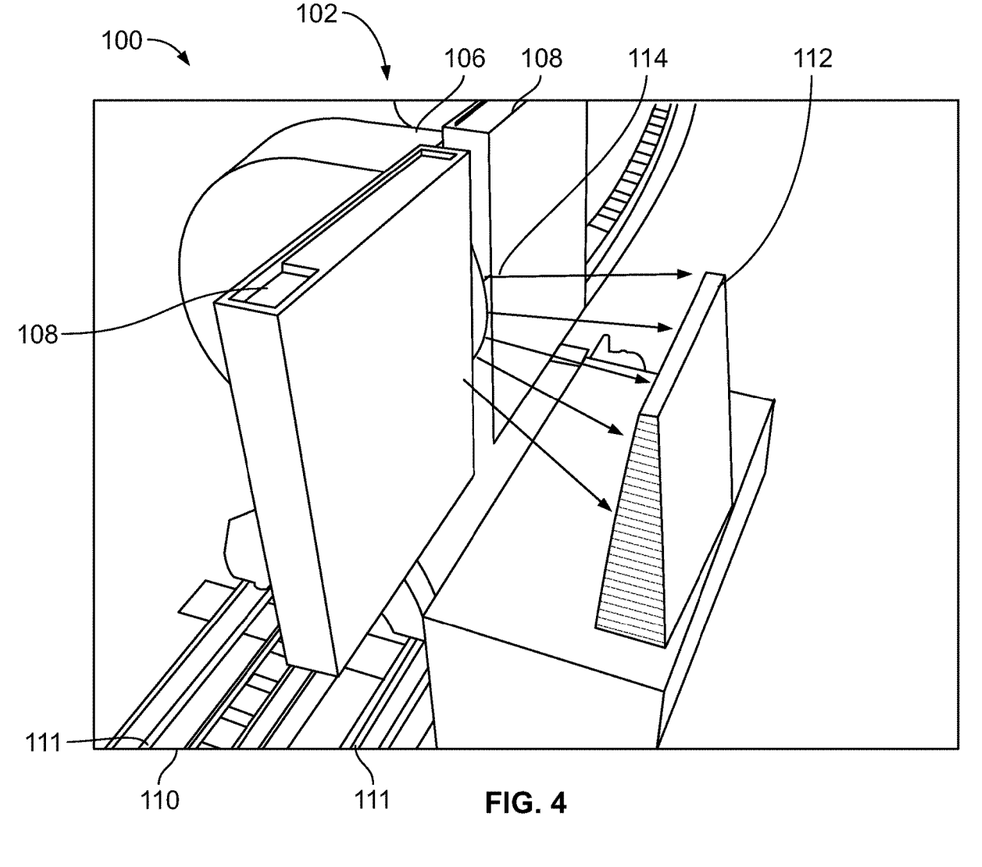
FIG. 4 illustrates a perspective view of a property detection system, according to an embodiment of the present disclosure.

FIG. 4 illustrates a perspective view of the property detection system 100. As shown, the property detection system 100 may include the X-ray assembly 102 mounted on the support 110, which may be in the form of one or more linear rails 111. Scatter detectors 108 are positioned on sides of the X-ray source 106. The scatter detectors 108 detect X-ray radiation scattered from the structure 112, such as Compton scattered X-rays. Compton scattering relates to inelastic scattering of a photon (such as an X-ray) by a charged particle, such as an electron, which typically leads to a decrease in energy of the photon. The wavelength of scattered X-ray radiation differs from the initially generated X-ray by the X-ray source 106. The X-ray source 106 may be configured to rotate the primary X-ray beam 114 with respect to the structure 112 over a sweep angle of the X-ray source 106.

The system 100 shown in FIG. 4 is but one example system configuration. As noted, the system 100 may be alternatively arranged so that the scatter detectors 108 detect forward scatter, instead of backscatter. Further, instead of the X-ray assembly 102 moving, the X-ray assembly 102 may be fixed in position, while the structure 112 is positioned on a moving support that moves the structure 112 in relation to the fixed X-ray assembly 102.

Figure 5:
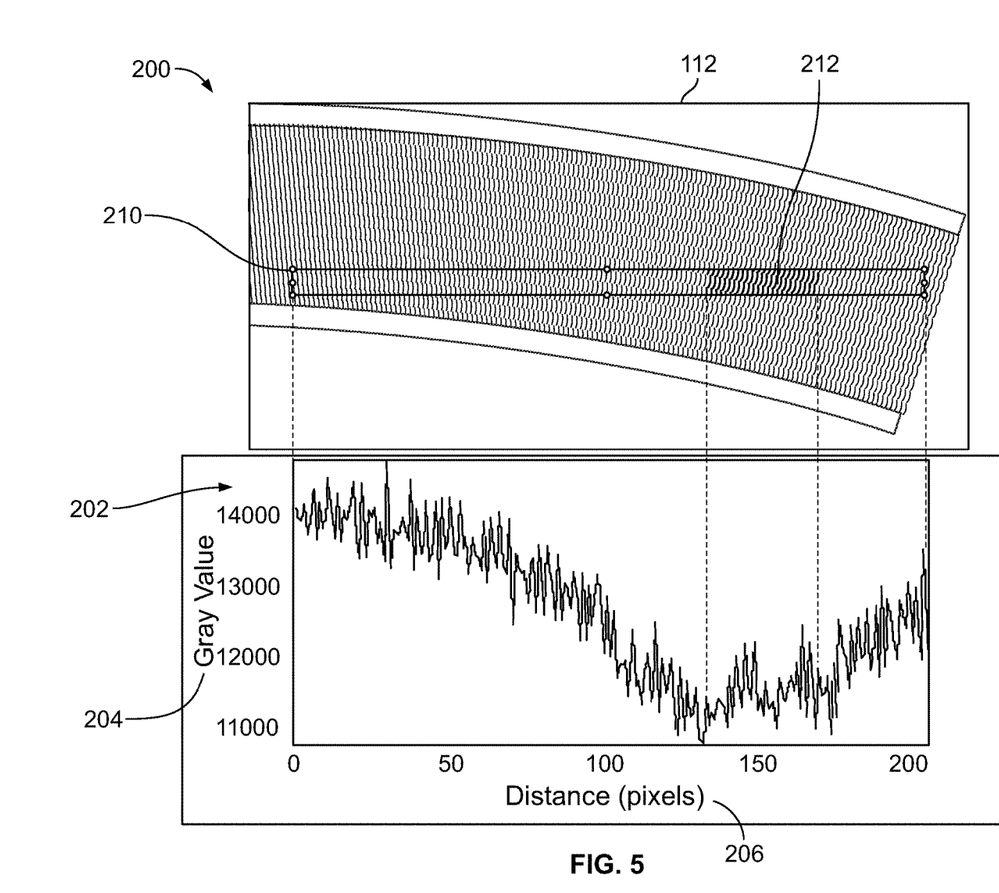
FIG. 5 illustrates an image of a structure in relation to a graph of gray values and distance on the structure, according to an embodiment of the present disclosure.

FIG. 5 illustrates an image 200 of the structure 112 in relation to a graph 202 of gray values 204 and distance 206 on the structure. Referring to FIGS. 1-2, 4, and 5, the control unit 104 may generate/reconstruct the image 200 based on the received X-ray scatter 116 over a length of the structure 112. In at least one embodiment, the image 200 may be an actually formed image of at least a portion of the structure. In at least one other embodiment, the image 200 may be or include data representing an image of at least a portion of the structure, whether viewable as an image or not. For example, a number of received X-ray photons of X-ray scatter 116 may be correlated with the gray value 204. An intensity of the gray value 204 may be directly (or alternatively, inversely) proportional to a number of X-ray photons. For example, a portion 210 of the structure 112 reflects the most amount of X-ray scatter 116, and therefore appears the brightest. Conversely, a portion 212 that varies from the portion 210 of the structure 112 reflects the least amount of X-ray scatter 116, and therefore appears the darkest. Alternatively, the relationship may be reversed, such that the portion 210 of the structure 112 appears darker than portion 212. Also, alternatively, instead of a gray scale, the image 200 may be color coded, such that different colors are assigned to different levels of variation.

As shown in FIG. 5, the structure 112 is generally normal from a length that corresponds from an end (0 pixels) to a distance that corresponds to about 50 pixels of the image 200. Variation 212 (such as damage) to the structure 112 is present at a distance that corresponds to 125 pixels to a distance that corresponds to about 200 pixels.

The pixel values are collected based on the detected scattered radiation. The pixel values may be compared to the calibration data to determine if any area of the structure 112 is above or below a predetermined variation threshold. For example, an area that has pixel values indicating an 85% variation level (in relation to the calibration data) may be flagged as unacceptable.

As shown and described, there are distinct differences in X-ray scatter counts between areas of the structure 112 having different physical properties (such as between burned and unburned areas, for example). Differences in physical properties (such as caused by heat variation) may be indicated by X-ray scatter count differences relative to one another. For example, an area of the structure 112 that has been changed by heat (for example, charred or burned) has a lower X-ray scatter count relative to an normal area of the structure 112. Heat variation beyond surface charring and color change may be detected by X-ray scatter count, thereby indicating a presence of incipient heat variation (for example, a change caused by heat before a resin within a composite begins to melt or char.

Optionally, a map of pixel values may be generated and/or displayed. The map may be or include an image (rendered or unrendered) of the structure 112 representing variations in a particular property (for example, fatigue, three-point bend, stiffness, and/or the like). In at least one embodiment, the map may provide a representation of Compton scatter in relation to one or more thermal and/or mechanical properties of a material that forms a structure.

Optionally, the pixel values and/or the map may be transferred to a Finite Element Analysis (FEA) model to assess one or more physical properties of the scanned structure 112. The FEA model may be beneficial when pixel values are within a margin of error in relation to a particular threshold, for example.

After the structure 112 has been analyzed to determine any areas of variation, the varied areas may be cut away, patched, or otherwise repaired. If a part of an aircraft, for example, is subjected to excessive heat, force, or wear, an inspecting agent may wish to know that removing a portion of the structure 112 removes the indicated varied area. Embodiments of the present disclosure provide systems and methods that ensure that a structure has consistent characteristics throughout, whether originally-manufactured or subsequently altered by, for example, patching. One particular application of the systems and methods described herein can ensure that a damaged area(s) has been fully removed and/or repaired. More generally, embodiments of the present disclosure provide systems and methods for efficiently detecting structural variations within a particular structure.

As described above, the control unit 104 may be used to control operation of the property detection system 100. As used herein, the term "control unit," "unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 104 may be or include one or more processors that are configured to control operation of the property detection system 100.

The control unit 104 is configured to execute a set of instructions that are stored in one or more storage elements (such as one or more memories), in order to process data. For example, the control unit 104 may include or be coupled to one or more memories. The storage elements may also store data or other information as desired or needed. The storage elements may be in the form of an information source or a physical memory element within a processing machine.

The set of instructions may include various commands that instruct the control unit 104 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the control unit 104. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 104 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 6:
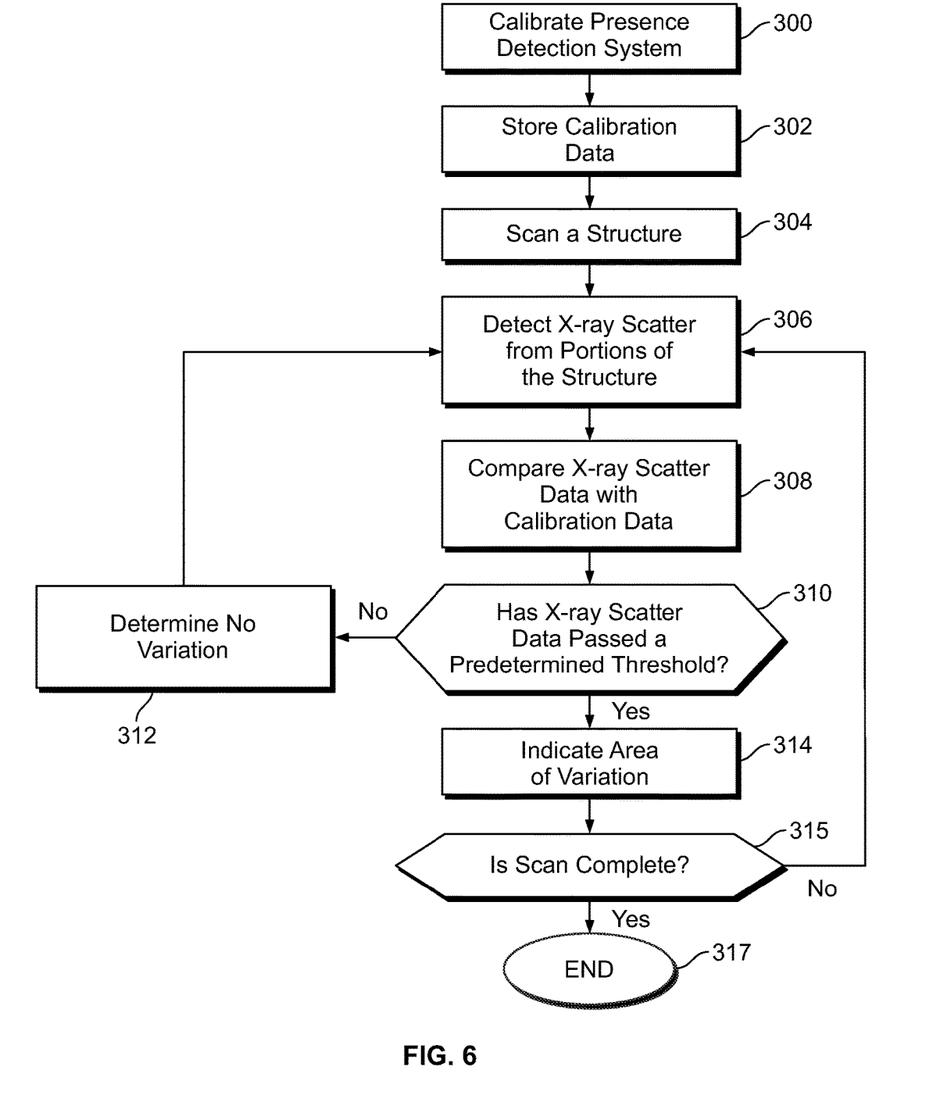
FIG. 6 illustrates a flow chart of a method of detecting one or more properties of a structure, according to an embodiment of the present disclosure.

FIG. 6 illustrates a flow chart of a method of detecting one or more properties of a structure, such as the structure 112. The control unit 104 (shown in FIGS. 1 and 2) may operate the property detection system 100 (shown in FIGS. 1 and 2, for example) according to the flow chart of FIG. 6. The method begins at 300, in which a property detection system 100 is calibrated. For example, an X-ray assembly (such as the X-ray assembly 102 shown in FIGS. 1 and 2) of the property detection system 100 may scan one or more test structures 120 (such as test coupons) having areas of altered physical properties. The X-ray assembly 102 scans the known tested areas and associates X-ray scatter data with each of the test structures 120 and/or regions thereof. The associations between the known tested areas and the X-ray scatter data may provide calibration data, such as in the form of a calibration curve, a lookup table, chart, algorithm, and/or the like. The calibration data is then stored at 302.

At 304, a structure 112 to be inspected is scanned by the X-ray assembly 100. At 306, X-ray scatter is detected from portions of the structure 112. In at least one embodiment, a two dimensional graph of the area of the structure being scanned may be formed (such as the graph 202 shown in FIG. 5). The graph may include an X-ray count axis (such as a gray value axis) and a distance axis (such as measured in pixels). At 308, X-ray scatter data related to the X-ray scatter is compared with the calibration data to determine areas in which physical properties differ. At 310, it is determined if value of the X-ray scatter data has passed (for example is above or below) a predetermined threshold (such as a percentage threshold indicating variation). If not, the method proceeds from 310 to 312, in which it is determined that no variation exists at that particular location of the structure. The method then returns to 306. If, however, the X-ray scatter data has passed (whether above or below) the predetermined threshold, the method proceeds from 310 to 314, in which the location of the structure is indicated (for example, flagged) as being damaged. At 315, it is determined if the scan of the structure is complete. If the scan is complete, the process ends at 317. If not, the method then returns to 306. In at least one embodiment, the X-ray scatter data and/or the calibration data may be transferred to a FEA model, which may be used to access localized strength reductions of the structure.

As described above, embodiments of the present disclosure provide systems and methods that are able to effectively detect localized areas of structural variation within a structure, such as a portion of an aircraft. Further, embodiments of the present disclosure provide systems and methods that are able to detect areas of incipient variation within a composite structure before the variation increases to an unacceptable level.

Embodiments of the present disclosure may be used to detect variations properties or characteristics of a structure other than damage. For example, embodiments of the present disclosure may be used to determine properties such as structural inconsistencies, anomalies, malformations, and/or the like.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A method of detecting one or more properties of a structure, wherein the method comprises:
   generating and storing calibration data determined from one or more test structures, wherein the one or more test structures are formed from a material that forms the structure;
   emitting X-ray radiation into the structure;
   detecting X-ray scatter from the structure; and
   determining the one or more properties of the structure based on the detected X-ray scatter and the calibration data, wherein the one or more properties are at least one of mechanical and thermal properties.

2. The method of claim 1, wherein the one or more properties include one or both of a density of the structure, or a variation level of polymeric bonds within the structure.

3. The method of claim 2, wherein the determining comprises associating differences in the density of the structure with levels of variation caused by heat energy.

4. The method of claim 1, further comprising comparing the X-ray scatter to a predetermined threshold to determine areas of variation within the structure.

5. The method of claim 1, further comprising generating a variation map from the X-ray scatter data.

6. The method of claim 1, wherein the generating and storing comprises generating and storing the calibration data as a calibration curve or lookup table.

7. The method of claim 1, wherein the X-ray scatter is one or both of X-ray backscatter or X-ray forward scatter.

8. A property detection system configured to detect one or more properties of a structure, wherein the property detection system comprises:
   an X-ray assembly including an X-ray source that emits X-ray radiation into the structure, and one or more scatter detectors that detect X-ray scatter that scatter from the structure, wherein the X-ray assembly scans one or more test structures that are formed from a material that forms the structure; and
   a control unit coupled to the X-ray assembly, wherein the control unit generates and stores calibration data determined from the one or more test structures, and wherein the control unit determines the one or more properties based on the X-ray scatter and the calibration data, wherein the one or more properties are at least one of mechanical and thermal properties.

9. The property detection system of claim 8, wherein the one or more test structures are formed of a material that forms the structure.

10. The property detection system of claim 8, wherein the one or more properties include one or both of a density of the structure, or a variation level of polymeric bonds within the structure.

11. The property detection system of claim 10, wherein the control unit associates differences in the density of the structure with levels of variation caused by heat energy.

12. The property detection system of claim 8, wherein the control unit compares the X-ray scatter to a predetermined threshold to determine areas of variation within the structure.

13. The property detection system of claim 8, wherein the calibration data is generated and stored as a calibration curve or lookup table.

14. The property detection system of claim 8, wherein the control unit generates a variation map from the X-ray scatter data.

15. The property detection system of claim 14, wherein the variation map comprises gray or color-coded values associated with a number of X-ray scatter photons detected by the one or more scatter detectors.

16. The property detection system of claim 8, wherein the X-ray source and the one or more scatter detectors are positioned to one side of the structure, and wherein the X-ray scatter is X-ray backscatter.

17. The property detection system of claim 8, wherein the structure is disposed between the X-ray source and the one or more scatter detectors, and wherein the X-ray scatter is X-ray front scatter.

18. A property detection system comprising:
   an X-ray assembly including an X-ray source that is configured to emit X-ray radiation into a structure, and one or more scatter detectors that are configured to detect X-ray scatter that scatter from the structure, wherein the X-ray assembly is configured to scan one or more test structures before emitting the X-ray radiation into the structure, wherein the one or more test structures are formed of a material that forms the structure; and
   a control unit coupled to the X-ray assembly, wherein the control unit is configured to:
      generate and store calibration data determined from the one or more test structures,
      determine variation within a structure by determining a density of the structure based on the detected X-ray scatter,
      associate differences in one or both of the density or polymeric bonds of the structure with levels of variation within the structure, and
      compare the X-ray scatter to a predetermined threshold to determine areas of variation within the structure.

19. The property detection system of claim 18, wherein the control unit is further configured to generate a variation map from the X-ray scatter data, wherein the variation map comprises gray or color-coded values associated with a number of X-ray scatter photons detected by the one or more scatter detectors.

\* \* \* \* \*